United States Patent [19]
Riedel et al.

[11] Patent Number: 6,156,296
[45] Date of Patent: *Dec. 5, 2000

[54] HAIR COSMETIC FORMULATIONS BASED ON PHYTOSTEROLS AND α-HYDROXYCARBOXYLIC ACIDS

[75] Inventors: Jan-Henric Riedel; Klaus Körbächer; Roland Hengel, all of Hamburg; Hartmut Schmidt-Lewerkühne, Schenefeld, all of Germany

[73] Assignee: Beiersdorf Aktiengesellschaft, Hamburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/807,972

[22] Filed: Mar. 3, 1997

[30] Foreign Application Priority Data

Mar. 7, 1996 [DE] Germany ............... 196 08 775

[51] Int. Cl.⁷ ............... A61K 7/06; A61K 7/075
[52] U.S. Cl. ............... 424/70.1; 424/63; 424/401; 424/704

[58] Field of Search ............... 424/70.1, 401, 424/63

[56] References Cited

U.S. PATENT DOCUMENTS

| 5,286,755 | 2/1994 | Kauffman | 514/944 |
| 5,874,074 | 2/1999 | Smith | 424/78.02 |
| 5,885,974 | 3/1999 | Danielov | |

FOREIGN PATENT DOCUMENTS

| 0273202 | 7/1988 | European Pat. Off. |
| 0587228 | 3/1994 | European Pat. Off. |
| 2313016 | 12/1976 | France |
| 347126 | 5/1931 | United Kingdom |
| 2078111 | 1/1982 | United Kingdom |

*Primary Examiner*—Richard L. Raymond
*Attorney, Agent, or Firm*—Norris, McLaughlin & Marcus, P.A.

[57] ABSTRACT

Hair cosmetic active compound combinations of
(a) one or more phytosterols and
(b) one or more α-hydroxycarboxylic acids and/or α-ketocarboxylic acids and/or salicylic acid.

22 Claims, No Drawings

HAIR COSMETIC FORMULATIONS BASED ON PHYTOSTEROLS AND α-HYDROXYCARBOXYLIC ACIDS

The present invention relates to hair cosmetic active compound combinations and formulations comprising such combinations. The present invention particularly relates to hair cosmetic active compound combinations and formulations for care of the hair and scalp. In a preferred embodiment, the present invention relates to active compound combinations and formulations which serve to strengthen the individual hair and/or to impart to the hairstyle overall hold and fullness.

Human hair can, in very general terms, be divided into the living part, the hair root, and the dead part, the hair shaft. The hair shaft in turn comprises the medulla, which, however, as a result of evolution has become unimportant to modern man and has receded, and is often completely absent from thin hair, and furthermore the cortex surrounding the medulla. And the cuticula enclosing the medulla and cortex in their entirety.

The cuticula in particular, but also the keratinous region between the cuticula and cortex, are exposed, as the outer casing of the hair, to particular stresses due to environmental influences, due to combing and brushing, and also due to hair treatment, especially colouring of the hair and shaping of the hair, for example permanent waving methods.

Under particularly aggressive stress, for example bleaching with oxidizing agents such as hydrogen peroxide, during which the pigments distributed in the cortex are destroyed by oxidation, the inside of the hair can also be impaired. If human hair is to be coloured permanently, only oxidizing hair-colouring methods are possible in practice. During oxidative hair colouring, the dyestuff chromophore is formed by reaction of precursors (phenols, aminophenols and less frequently also diamines) and bases (usually p-phenylenediamine) with the oxidizing agent, usually hydrogen peroxide. Hydrogen peroxide concentrations of about 6% are usually used here.

It is usually assumed that, in addition to the colouring action, a bleaching action by the hydrogen peroxide also takes place. In human hair coloured oxidatively, as in bleached hair, microscopic holes are detectable at the places where melanin granules existed. The fact is that the oxidizing agent hydrogen peroxide reacts not only with the colour precursors but also with the hair substance, and in doing so can in certain circumstances cause damage to the hair.

Washing the hair with aggressive surfactants can also expose the hair to stress, and at least impair its appearance or the appearance of the hairstyle overall. For example, certain water-soluble hair constituents (for example urea, uric acid, xanthine, keratin, glycogen, citric acid and lactic acid) can be leached out by washing the hair.

For these reasons, in some cases hair-care cosmetics which are intended to be rinsed out again after acting on the hair and in some cases those which are to remain on the hair have been used for a considerable length of time. The latter can be formulated such that they not only serve to care for the individual hair, but also improve the appearance of the hairstyle overall, for example by imparting to the hair more fullness, fixing the hairstyle over a relatively long period of time or improving its ease of styling.

For example, the combability of the hair can be improved decisively by quaternary ammonium compounds. Such compounds attach to the hair and are often still detectable on the hair after the hair has been washed several times.

However, the prior art has lacked active compounds and formulations which could provide damaged hair with care in a satisfactory manner. Formulations which have been said to give the hairstyle fullness have often also proved inadequate, and at least were unsuitable for use as hair-care formulations. For example, formulations of the prior art which fix the hairstyle generally comprise viscous constituents, which run the risk of causing a feeling of tackiness, which often has to be compensated by skilful formulation.

The object was therefore to remedy the disadvantages of the prior art.

It has been found, astonishingly, that hair cosmetic active compound combinations of (a) one or more phytosterols and (b) one or more α-hydroxycarboxylic acids and/or α-ketocarboxylic acids and/or salicylic acid eliminate the disadvantages of the prior art.

The active compound combinations according to the invention and formulations comprising these active compound combinations care for hair which has been damaged or strained by environmental influences or prevent such environmental influences. Furthermore, the active compound combinations according to the invention and formulations comprising these active combinations improve the combability of the hair without addition of active compounds containing quaternary nitrogen groups ("quats") being necessary.

Phytosterols are sterols which are found in plants and yeasts. The latter are also called mycosterols. In contrast to animal sterols, phytosterols are substituted by a $C_1$ or $C_2$ radical in the C-24 position and usually have a double bond in the C-22 position.

Examples of phytosterols are:

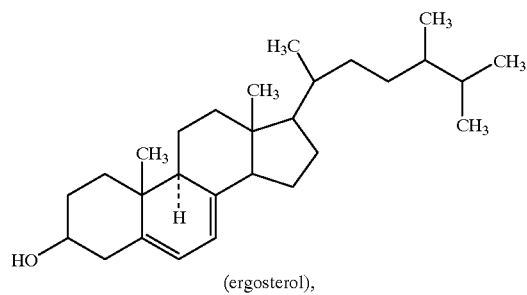

(ergosterol),

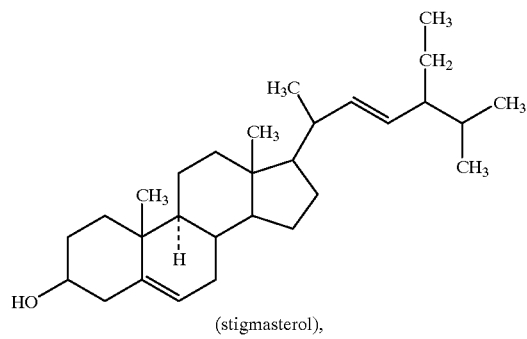

(stigmasterol),

-continued

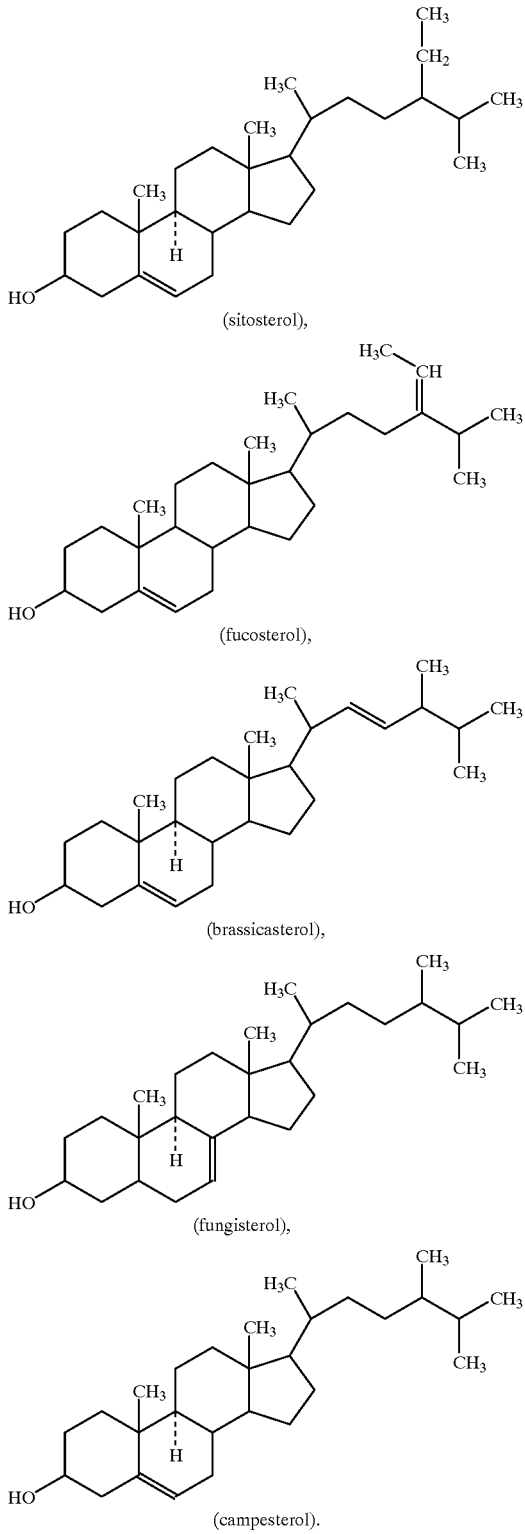

(sitosterol), (fucosterol), (brassicasterol), (fungisterol), (campesterol).

All the phytosterols to be used according to the invention have a more or less large number of optical isomers which will not be listed here individually but which have proved advantageous where their cosmetic acceptability is not in question.

Preferred phytosterols are sitosterol, campesterol and stigmasterol.

Formulations according to the invention advantageously comprise 0.01–25% by weight of one or more phytosterols, preferably 0.1–20% by weight, in particular 1–10% by weight, in each case based on the total weight of the formulations.

According to the invention, the α-hydroxycarboxylic acid or acids is or are advantageously chosen from the group consisting of substances of the general formula

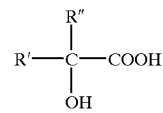

and/or the α-ketocarboxylic acid or acids is or are chosen from the group consisting of substances of the general formula

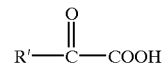

wherein in each case R' and R" independently of one another are chosen from the group consisting of
(a1) H-,
(a2) branched or unbranched $C_{1-25}$-alkyl-,
(a3) branched or unbranched $C_{1-25}$-alkyl- which is substituted by one or more carboxyl groups and/or hydroxyl groups and/or aldehyde groups and/or oxo groups (keto groups),
(a4) phenyl-,
(a5) phenyl- which is substituted by one or more carboxyl groups and/or hydroxyl groups and/or branched and/or unbranched $C_{1-25}$-alkyl groups,
or wherein the α-carbon atom of the α-hydroxycarboxylic acid, together with R' and R", forms an
(a6) unsubstituted cycloalkyl group having 3 to 7 ring atoms or a
(a7) cycloalkyl group having 3 to 7 ring atoms which is substituted by one or more carboxyl groups and/or hydroxyl groups and/or oxo groups (keto groups) and/or branched and/or unbranched $C_{1-25}$-alkyl groups and
wherein the α-hydroxycarboxylic acid or the α-hydroxycarboxylic acids or the α-ketocarboxylic acid or the α-ketocarboxylic acids can be present, where appropriate, in the form of their physiologically tolerated salts and/or ethyl esters and/or methyl esters.

Salicylic acid (also called 2-hydroxybenzoic acid or spirolyl acid) is characterized by the structure of the formula

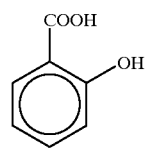

As is known, salicylic acid has an antibacterial and keratolytic action and is a constituent of some cosmetic or pharmaceutical formulations.

The α-hydroxycarboxylic acids according to the invention are advantageously chosen from the following classes of substances:
(a2) α-hydroxy-fatty acids, these in turn being particularly advantageously chosen from the group consisting of $C_{10-18}$-alkylcarboxylic acids, (a3) α-hydroxy-sugar acids, aliphatic α-hydroxy-fruit acids,
(a4) unsubstituted aromatic α-hydroxycarboxylic acids (for example mandelic acid) and
(a5) substituted aromatic α-hydroxycarboxylic acids. The α-hydroxy-fatty acids falling under item (a2) are particularly advantageously chosen from the group consisting of α-hydroxycarboxylic acids according to the formula

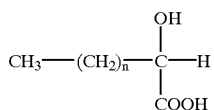

and/or
α-hydroxy-isocarboxylic acids according to the formula

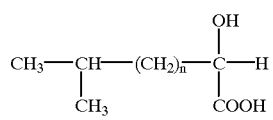

and/or
α-hydroxy-anteisocarboxylic acids according to the formula

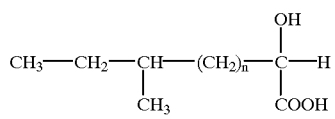

wherein n in each case is a number from 7 to 31.

It is particularly advantageous in the context of the present invention to use α-hydroxycarboxylic acids which are $C_{16}$ substances, that is to say which carry a branched or unbranched $C_{14}H_{29}$ chain on the α-carbon atom.

It is furthermore advantageous to use mixtures of such aliphatic α-hydroxy carboxylic acids, in particular in the form of wool wax acid mixtures, in which the content of α-hydroxycarboxylic acids is 20–30% by weight, based on the total composition.

The α-hydroxy-sugar acids falling under item (a3) are particularly advantageously chosen from the group consisting of
aldonic acids, for example gluconic acid and galactonic acid
aldaric acids, for example glucaric acid and galactaric acid (and also the fruit acid tartaric acid, which likewise falls under the definition of aldaric acid)
uronic acids, for example glucuronic acid and galacturonic acid, and
glyceric acid.

The aliphatic α-hydroxy-fruit acids falling under item (a3) are particularly advantageously chosen from the group consisting of malic acid, lactic acid, citric acid and tartaric acid.

Malic acid (hydroxysuccinic acid) is characterized by the following chemical structure:

HOOC—CH$_2$—CH(OH)—COOH

Lactic acid (2-hydroxypropanoic acid) is characterized by the following chemical structure:

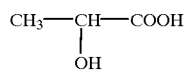

Citric acid (2-hydroxy-1,2,3-propanetricarboxylic acid) is characterized by the following chemical structure:

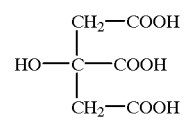

As is known, citric acid is used for buffering cosmetic and/or dermatological formulations, and also as a synergist for antioxidants in skin and hair cosmetic.

Tartaric acid (dihydroxysuccinic acid) is characterized by the following chemical structure:

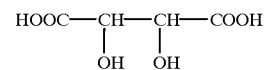

The preferred α-ketocarboxylic acid is pyruvic acid (α-oxopropanoic acid). It is distinguished by the following structure:

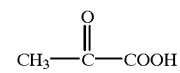

For use, the cosmetic and dermatological formulations according to the invention are applied to the skin and/or the hair in an adequate amount in the manner customary for cosmetics.

Formulations according to the invention furthermore advantageously comprise, in addition to an active content of active compound combinations according to the invention, customary active compounds, constituents, additives and/or auxiliaries.

It is particularly advantageous to add chitosan to the formulations according to the invention.

Chitosan is characterized by the following structural formula:

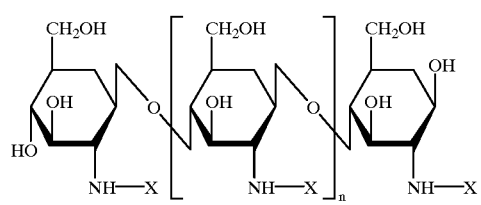

where n assumes values up to about 2,000 and X is either the acetyl radical or hydrogen. Chitosan is formed by deacetylation and partial depolymerization (hydrolysis) of chitin, which is characterized by the structural formula

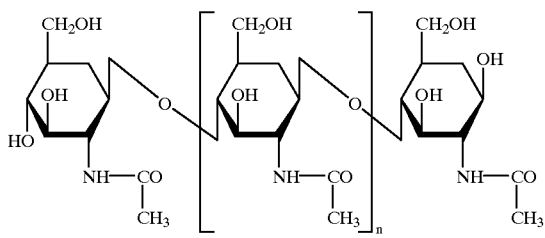

Chitin is an essential constituent of the ectoskeleton ['οχιτων=Greek: armoured robe] of arthropods (for example insects, crustaceans, spiders) and is also found in supporting tissues of other organisms (for example molluscs, algae, fungi).

Chitosan is a raw material known in hair care. It is suitable, preferably as the chitin on which it is based, as a thickener or stabilizer and improves the adhesion and water resistance of polymeric films. Representative of large number of references in locations of the prior art is: H. P.Fiedler, "Lexikon der Hilfsstoffe für Pharmazie, Kosmetik und angrenzende Gebiete" [Dictionary of auxiliaries for pharmacy, cosmetics and related fields], 3rd edition 1989, Editio Cantor, Aulendorf, page 293, keyword "Chitosan".

Chitosans which are preferred according to the invention are those having a degree of deacetylization of >60%, in particular >80%. Among these, particularly preferred chitosans are those of which a 1% strength aqueous solution has a viscosity of 4,500–5,500 mpas (Brookfield, spindle 5, 10 rpm), in particular 5,000 mPas.

The formulations according to the invention advantageously comprise 0.05–5% by weight of chitosan, preferably 0.5–2% by weight, in particular 1% by weight, in each case based on the total weight of the formulations.

Although it is possible, according to the invention, to dispense with quaternary nitrogen compounds ("quats"), their addition, where appropriate, may prove to be advantageous.

Suitable film-forming polymers with at least partly quaternized nitrogen groups (called "film-forming agents" in the following) are preferably those which are chosen from the group consisting of substances which, according to INCI nomenclature (International Nomenclature Cosmetic Ingredient), carry the name "polyquaternium", for example:

| | |
|---|---|
| polyquaternium-2 | Chemical Abstracts No. 63451-27-4, for example Mirapol ® A-15 |
| polyquaternium-5 | Copolymer of acrylamide and β-methacryloxyethyltrimethyl-ammonium methosulphate, CAS No. 26006-22-4 |
| polyquaternium-6 | Homopolymer of N,N-dimethyl-N-2-propenyl-2-propen-1-aminium chloride, CAS No. 26062-79-3, for example Merquat ® 100 |
| polyquaternium-7 | N,N-Dimethyl-N-2-propenyl-2-propen-1-aminium chloride, polymer with 2-propenamide, CAS No. 26590-05-6, for example Merquat ® S |
| polyquaternium-10 | Quaternary ammonium salt of hydroxy-ethylcellulose, CAS No. 53568-66-4, 55353-19-0, 54351-50-7, 68610-92-4, 81859-24-7, for example Celquat ® SC-230M, |
| polyquaternium-11 | Vinylpyrrolidone/dimethylaminoethyl methacrylate copolymer/Diethyl sul-phate reaction product, CAS No. 53633-54-8, for example Gafquat ® 755N |
| polyquaternium-16 | Vinylpyrrolidone/vinylimidazolinium methochloride copolymer, CAS No. 29297-55-0, for example Luviquat ® HM 552 |
| polyquaternium-17 | CAS No. 90624-75-2, for example Mirapol ® AD-1 |
| polyquaternium-19 | Quaternized water-soluble polyvinyl alcohol |
| polyquaternium-20 | Water-dispersible quaternized poly-vinyl octadecyl ether |
| polyquaternium-21 | Polysiloxane/polydimethyl-dimethyl-ammonium acetate copolymer, for example Abil ® B 9905 |
| polyquaternium-22 | Dimethyldiallylammonium chloride/acrylic acid copolymer, CAS No. 53694-7-0, for example Merquat ® 280 |
| polyquaternium-24 | Polymeric quaternary ammonium salt of hydroxyethylcellulose, reaction product with an epoxide substituted by lauryldimethylammonium, CAS No. 107987-23-5, for example Quatrisoft ® LM-200 |
| polyquaternium-28 | Vinylpyrrolidone/methacrylamido-propyltrimethylammonium chloride copolymer, for example Gafquat ® HS-100 |
| polyquaternium-29 | for example Lexquat ® CH |
| polyquaternium-31 | CAS No. 136505-02-7, for example Hypan ® QT 100 |
| polyquaternium-32 | N,N,N-Trimethyl-2-[(2-methyl-1-oxo-2-propenyl)oxyl]ethanaminium chloride, polymer with 2-propenamide, CAS No. 35429-19-7 |
| polyquaternium-37 | CAS No. 26161-33-1 |

The film-forming agent which is preferred according to the invention is polyquaternium-11.

Formulations according to the invention advantageously comprise 0.2–50% by weight of one or more film-forming agents, preferably 5–30% by weight, in particular 10–25% by weight, in each case based on the total weight of the formulations.

The cosmetic and dermatological formulations according to the invention can comprise cosmetic auxiliaries such as are usually used in such formulations, for. example preservatives, bactericides, perfumes, substances for preventing foaming, dyestuffs, pigments which have a colouring action, thickeners, surface-active substances, emulsifiers, softening, humidifying and/or humectant substances, fats, oils, waxes or other customary constituents of a cosmetic or dermatological formulation, such as alcohols, polyols, polymers, foam stabilizers, electrolytes, organic solvents or silicone derivatives.

In particular, the cosmetic and dermatological formulations according to the invention can advantageously comprise antioxidants.

Favourable antioxidants which can be used in accordance with the invention are all antioxidants which are suitable or customary for cosmetic and/or dermatological applications.

The antioxidants are advantageously chosen from the group consisting of amino acids (for example glycine, histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to μmol/kg), and furthermore (metal) chelators (for example α-hydroxy-fatty acids, palmitic acid, phytic acid and lactoferrin), α-hydroxy acids (for example citric acid, lactic acid and malic acid), humic acid, bile acid, bile extracts, bilirubin, biliverdin, EDTA and EGTA and derivatives thereof, unsaturated fatty acids and derivatives thereof (for example γ-linolenic acid, linoleic acid and oleic acid), folic acid and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoin resin, rutic acid and derivatives thereof, ferulic acid and derivatives thereof, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO and $ZnSO_4$), selenium and derivatives thereof (for example seleniummethionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

The amount of antioxidants (one or more compounds) in the formulations is preferably 0.001 to 30% by weight, particularly preferably 0.05–20% by weight, in particular 1–10% by weight, based on the total weight of the formulation.

If appropriate, the aqueous formulations according to the invention advantageously comprise alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of so-called Carbopols, for example Carbopols of types 980, 981, 1382, 2984 and 5984, in each case individually or in combination.

Gels according to the invention usually comprise alcohols of low C number, for example ethanol, isopropanol, 1,2-propanediol, glycerol and water, or an above-mentioned oil in the presence of a thickener, which is preferably silicon dioxide or an aluminium silicate in oily-alcoholic gels and is preferably a polyacrylate in aqueous-alcoholic or alcoholic gels.

Formulations according to the invention can furthermore advantageously comprise substances which absorb UV radiation in the UVB range, the total amount of filter substances being, for example, 0.01% by weight to 30% by weight, preferably 0.5 to 10% by weight, in particular 1.0 to 6.0% by weight, based on the total weight of the formulations, in order to provide cosmetic formulations which protect the hair or skin from the entire range of ultraviolet radiation. They can also be used as sunscreen compositions for the hair or skin, in particular the scalp.

If the emulsions according to the invention comprise UVB filter substances, these can advantageously be water-soluble. Advantageous water-soluble UVB filters are, for example:

salts of 2-phenylbenzimidazole-5-sulphonic acid, such as its sodium, potassium or its triethanolammonium salt and 2-phenylbenzimidazole-5-sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl) benzenesulphonic acid, 2-methyl-S-(2-oxo-3-bornylidenemethyl)benzenesulphonic acid and their salts.

It may also be advantageous to add UVA filters which have previously usually been contained in cosmetic formulations to formulations according to the invention. The amounts used for the UVB combination can be employed.

Cosmetic and dermatological formulations according to the invention are, for example, shampooing compositions, formulations which are used when rinsing the hair before or after shampooing, before or after permanent wave treatment, or before or after colouring or bleaching the hair, formulations for blow-drying or setting the hair, formulations for colouring or bleaching, a styling and treatment lotion, a hair lacquer or a permanent wave composition.

The cosmetic and dermatological formulations comprise active compounds and auxiliaries such as are usually used for this type of formulation for hair care and hair treatment. The auxiliaries used are preservatives, surface-active substances, substances for preventing foaming, thickeners, emulsifiers, fats, oils, waxes, organic solvents, bactericides, perfumes, dye-stuffs or pigments, the function of which is to colour the hair or the cosmetic or dermatological formulation itself, electrolytes and substances against the hair becoming greasy.

Electrolytes in the context of the present invention are to be understood as meaning water-soluble alkali metal, ammonium, alkaline earth metal (including magnesium) and zinc salts of inorganic anions and any desired mixtures of such salts, where it must be ensured that these salts are distinguished by pharmaceutical or cosmetic acceptability.

The anions according to the invention are preferably chosen from the group consisting of chlorides, sulphates and hydrogen sulphates, phosphates, hydrogen phosphates and linear and cyclic oligophosphates and carbonates and bicarbonates.

Cosmetic formulations which are a shampooing composition preferably comprise at least one anionic, nonionic or amphoteric surface-active substance or else mixtures of such substances, chlorogenic acid in an aqueous medium and auxiliaries such as are usually used for this purpose. The surface-active substance or the mixtures of these substances can be present in the shampooing composition in a concentration of between 1% by weight and 50% by weight.

If the cosmetic or dermatological formulations are in the form of a lotion which is rinsed out and is used, for example, before or after bleaching, before or after shampooing, between two shampooing steps or before or after permanent wave treatment, they are, for example, aqueous or aqueous-alcoholic solutions which comprise, if appropriate, surface-active substances, the concentration of which can be between 0.1 and 10% by weight, preferably between 0.2 and 5% by weight.

A cosmetic formulation in the form of a lotion which is not rinsed out, in particular a lotion for setting the hair, a lotion which is used when blow-drying the hair or a styling and treatment lotion, is in general an aqueous, alcoholic or aqueous-alcoholic solution and comprises the combinations according to the invention.

According to the invention, cosmetic formulations for treatment and care of hair can be in the form of gels which comprise organic thickeners, for example gum arabic, xanthan gum, sodium alginate and cellulose derivatives, preferably methylcellulose, hydroxymethylcellulose, hydroxyethylcellulose, hydroxypropylcellulose and hydroxypropylmethylcellulose, or inorganic thickeners, for example aluminium silicates, such as, for example, bentonite, or a mixture of polyethylene glycol and polyethylene glycol stearate or distearate. The gel comprises the thickener, for example, in an amount of between 0.1 and 30% by weight, preferably between 0.5 and 15% by weight.

Aqueous cosmetic cleansing compositions according to the invention, or cleansing composition concentrates. that are low in or free from water and are intended for aqueous cleansing, can comprise anionic, nonionic and/or amphoteric surfactants, for example conventional soaps, for example fatty acid salts of sodium, alkyl sulphates, alkyl ether-sulphates, alkane- and alkylbenzenesulphonates, sulphoacetates, sulphobetaines, sarcosinates, amidosulphobetaines, sulphosuccinates, sulphosuccinic acid half-esters, alkyl ether-carboxylates, protein-fatty acid condensates, alkylbetaines and amidobetaines, fatty acid alkanolamides and polyglycol ether derivatives.

Cosmetic formulations which are cosmetic cleansing formulations for the hair or scalp can be in a liquid or solid form. They preferably comprise at least one anionic, nonionic or amphoteric surface-active substance or mixtures thereof, if appropriate an electrolyte and auxiliaries such as are usually used for this purpose. The surface-active substance can be present in the cleansing formulations in a concentration of between 1 and 94% by weight, based on the total weight of the formulations.

If appropriate, the compositions according to the invention comprise the additives customary in cosmetics, for example perfume, thickeners, dyestuffs, deodorants, antimicrobial substances, re-oiling agents, complexing and sequestering agents, pearlescent agents, plant extracts, vitamins, active compounds and the like.

The following examples are intended to illustrate the present invention without limiting it. All the amounts, contents and percentage are based on the weight and the total amount or on the total weight of the formulations, unless stated otherwise.

EXAMPLES

|  | I | II | III | IV |
|---|---|---|---|---|
| 1) Hair lotion |  |  |  |  |
| Alcohol | 50 | 50 | 50 | 50 |
| Lactic acid | 0.50 | 1.0 | 1.5 | 2.0 |
| Campesterol | 0.50 | — | — | — |

-continued

|  | I | II | III | IV |
|---|---|---|---|---|
| Ergosterol | — | 0.50 | — | — |
| Sitosterol | — | — | 0.50 | — |
| Stigmasterol | — | — | — | 0.50 |
| Preservatives, perfume, dyestuffs | q.s. | q.s. | q.s. | q.s. |
| Water, completely desalinated | to 100.00 | to 100.00 | to 100.00 | to 100.00 |
| 2) Hair treatment course |  |  |  |  |
| Hydroxypropylmethylcellulose | 0.50 | 0.50 |  |  |
| Glycerol | 6.50 | 6.50 |  |  |
| Cetearyl alcohol | 3.50 | 3.50 |  |  |
| Glyceryl stearate | 3.00 | 3.00 |  |  |
| Lactic acid | 2.00 | 3.00 |  |  |
| Ergosterol | 0.50 | — |  |  |
| Stigmasterol |  | 1.00 |  |  |
| Preservatives, perfume, dyestuffs | q.s. | q.s. |  |  |
| Water, completely desalinated | to 100.00 | to 100.00 |  |  |
| 3) Hair rinse |  |  |  |  |
| Glycerol | 5.00 | 5.00 |  |  |
| Hydroxyethylcellulose | 0.20 | 0.20 |  |  |
| Cetearyl alcohol | 5.00 | 5.00 |  |  |
| Lactic acid | 1.50 | 2.00 |  |  |
| Campesterol | 0.50 | — |  |  |
| Stigmasterol |  | 0.90 |  |  |
| Preservatives, perfume, dyestuffs | q.s. | q.s. |  |  |
| Water, completely desalinated | to 100.00 | to 100.00 |  |  |
| 4) Shampoo |  |  |  |  |
| Sodium laureth-sulphate | 12.00 | 12.00 |  |  |
| Cocoamidopropylbetaine | 3.00 | 3.00 |  |  |
| Disodium laureth-sulphosuccinate | 1.50 | 1.50 |  |  |
| Lactic acid | 2.00 | 3.00 |  |  |
| Sitosterol | 1.00 | — |  |  |
| Campesterol |  | 1.50 |  |  |
| Pearlescent agent | 4.00 | 4.00 |  |  |
| Preservatives, perfume, dyestuffs, thickeners | q.s. | q.s. |  |  |
| Water, completely desalinated | to 100.00 | to 100.00 |  |  |

What is claimed is:

1. A method of caring for the hair, said method comprising administering to the hair an effective amount therefor of a cosmetic composition comprising an effective amount therefor of a combination of:
   a) one or more phytosterols; and
   b) one or more carboxylic acids selected from the group consisting of α-hydroxycarboxylic acids, α-ketocarboxylic acids, and salicylic acid.

2. A method of caring for the hair, said method comprising administering to the hair and the scalp an effective amount therefor of a cosmetic composition comprising an effective amount therefor of a combination of:
   a) one or more phytosterols; and
   b) one or more carboxylic acids selected from the group consisting of α-hydroxycarboxylic acids, α-ketocarboxylic acids, and salicylic acid.

3. The method according to claim 1, wherein the phytosterol or phytosterols is or are selected from the group consisting of sitosterols, campesterols, and stigmasterols.

4. The method according to claim 1, wherein the composition comprises 0.05–5% by weight of phytosterol or phytosterols based on the total weight of the composition.

5. The method according to claim 4, wherein the composition comprises 0.5–2% by weight of phytosterol or phytosterols based on the total weight of the composition.

6. The method according to claim 5, wherein the composition comprises about 1% by weight of phytosterol or phytosterols based on the total weight of the composition.

7. The method according to claim 1, wherein the composition comprises 0.01–25% by weight of said carboxylic acid or carboxylic acids based on the total weight of the composition.

8. The method according to claim 7, wherein the composition comprises 0.1–20% by weight of said carboxylic acid or carboxylic acids based on the total weight of the composition.

9. The method according to claim 8, wherein the composition comprises 1–10% by weight of said carboxylic acid or carboxylic acids based on the total weight of the composition.

10. The method according to claim 1, wherein the composition further comprises chitosan.

11. The method according to claim 1, wherein the composition further comprises a substance that absorbs ultraviolet (UV) radiation in the UVB range.

12. The method according to claim 2, wherein the phytosterol or phytosterols is or are selected from the group consisting of sistosterols, campesterols, and stigmasterols.

13. The method according to claim 2, wherein the composition comprises 0.05–5% by weight of phytosterol or phytosterols based on the total weight of the composition.

14. The method according to claim 13, wherein the composition comprises 0.5–2% by weight of phytosterol or phytosterols based on the total weight of the composition.

15. The method according to claim 14, wherein the composition comprises about 1% by weight of phytosterol or phytosterols based on the total weight of the composition.

16. The method according to claim 2, wherein the composition comprises 0.01–25% by weight of said carboxylic acid or carboxylic acids based on the total weight of the composition.

17. The method according to claim 16, wherein the composition comprises 0.1–20% by weight of said carboxylic acid or carboxylic acids based on the total weight of the composition.

18. The method according to claim 17, wherein the composition comprises 1–10% by weight of said carboxylic acid or carboxylic acids based on the total weight of the composition.

19. The method according to claim 2, wherein the composition further comprises chitosan.

20. The method according to claim 2, wherein the composition further comprises a substance that absorbs ultraviolet (UV) radiation in the UVB range.

21. A method of strengthening individual hairs, imparting overall hold and fullness to a hairstyle, and/or improving the combability of hair, said method comprising administering to the hair an effective amount therefor of a cosmetic composition comprising an effective amount therefor of a combination of:

a) one or more phytosterols; and b) one or more carboxylic acids selected from the group consisting of α-hydroxycarboxylic acids, α-ketocarboxylic acids, and salicylic acid.

22. A method of strengthening individual hairs, imparting overall hold and fullness to a hairstyle, and/or improving the combability of hair, said method comprising administering to the hair and the scalp an effective amount therefor of a cosmetic composition comprising an effective amount therefor of a combination of:

a) one or more phytosterols; and b) one or more carboxylic acids selected from the group consisting of α-hydroxycarboxylic acids, α-ketocarboxylic acids, and salicylic acid.

* * * * *